(12) United States Patent
Amling et al.

(10) Patent No.: US 7,821,530 B2
(45) Date of Patent: *Oct. 26, 2010

(54) INTELLIGENT CAMERA HEAD

(75) Inventors: Marc R. Amling, Santa Barbara, CA (US); David Chatenever, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 12/250,939

(22) Filed: Oct. 14, 2008

(65) Prior Publication Data

US 2009/0096894 A1    Apr. 16, 2009

Related U.S. Application Data

(63) Continuation of application No. 10/033,316, filed on Dec. 28, 2001, now Pat. No. 7,471,310.

(51) Int. Cl.
*H04N 5/232* (2006.01)
*A61B 1/04* (2006.01)

(52) U.S. Cl. .................. 348/72; 348/211.14; 600/118

(58) Field of Classification Search .......... 348/65, 348/72–74, 211.14; 600/109, 112, 118, 129, 600/175

See application file for complete search history.

(56) References Cited

U.S. PATENT DOCUMENTS

| | | | |
|---|---|---|---|
| 4,963,960 A | 10/1990 | Takami | |
| 5,007,408 A | 4/1991 | Ieoka | |
| 5,010,876 A | 4/1991 | Henley et al. | |
| 5,239,983 A | 8/1993 | Katsurada | |
| 5,242,315 A | 9/1993 | O'Dea | |
| 5,419,717 A | 5/1995 | Abendschein et al. | |
| 5,563,655 A * | 10/1996 | Lathrop | 348/231.9 |
| 5,575,757 A | 11/1996 | Kennedy et al. | |
| 5,702,345 A | 12/1997 | Wood et al. | |
| 5,852,697 A | 12/1998 | Williams et al. | |
| 5,896,166 A | 4/1999 | D'Alfonso et al. | |
| 5,978,651 A | 11/1999 | Eto et al. | |
| 6,046,769 A | 4/2000 | Ikeda et al. | |
| 6,219,091 B1 | 4/2001 | Yamanaka et al. | |

(Continued)

FOREIGN PATENT DOCUMENTS

EP         0534198 A2    3/1993

(Continued)

OTHER PUBLICATIONS

European Search Report, EP02029053, Feb. 4, 2004, 3 pages.

(Continued)

*Primary Examiner*—David L Ometz
*Assistant Examiner*—Dillon Durnford-Geszvain
(74) *Attorney, Agent, or Firm*—St. Onge Steward Johnston & Reens LLC

(57) ABSTRACT

A video imaging system that minimizes the effect of EMI on the image data, provides a small, lightweight easy to use camera head, permitting interchangeable use of a variety of intelligent camera heads with a single camera control unit, and allows the utilization of new camera heads with new functions as they become available without having to replace the existing CCU.

9 Claims, 7 Drawing Sheets

U.S. PATENT DOCUMENTS

| | | |
|---|---|---|
| 6,295,082 B1 | 9/2001 | Dowdy et al. |
| 6,313,868 B1 | 11/2001 | D'Alfonso et al. |
| 6,390,972 B1 | 5/2002 | Speier et al. |
| 6,449,007 B1 | 9/2002 | Yokoyama |
| 6,573,931 B1 | 6/2003 | Horii et al. |
| 6,638,212 B1 | 10/2003 | Oshima |
| 6,707,490 B1 | 3/2004 | Kido et al. |
| 6,753,901 B1 | 6/2004 | Takahashi et al. |
| 6,836,290 B1 | 12/2004 | Chung et al. |
| 6,870,566 B1 | 3/2005 | Koide et al. |
| 6,975,351 B2 | 12/2005 | Ikeda et al. |
| 7,316,646 B2 | 1/2008 | Amling et al. |
| 7,471,310 B2 * | 12/2008 | Amling et al. ................ 348/72 |

FOREIGN PATENT DOCUMENTS

| | | |
|---|---|---|
| EP | 0669752 A2 | 8/1995 |
| FR | 2767004 A1 | 2/1999 |
| WO | 9955082 A1 | 10/1999 |

OTHER PUBLICATIONS

Interface Circuits for TIA/EIA-644 (LVDS) Design Notes, Copyright 1998, Texas Instruments Incorporated.

* cited by examiner

INTELLIGENT CAMERA HEAD

CROSS-REFERENCE TO RELATED APPLICATIONS

The present application is a continuation of and claims priority from U.S. patent application Ser. No. 10/033,316, filed Dec. 28, 2001, now U.S. Pat. No. 7,471,310, the content of which is incorporated herein by reference.

FIELD OF THE INVENTION

The invention relates to a camera head having components permitting its interchangeable use with a variety of camera control units.

BACKGROUND OF THE INVENTION

The field of video endoscopy, to which the present invention generally relates, includes medical diagnostic and therapeutic disciplines that utilize endoscopes to penetrate and view otherwise inaccessible body cavities utilizing minimally invasive surgical procedures. Coupling of video imaging cameras (incorporating solid-state imagers) to endoscopes, for image reproduction, has become standard within the field. Endoscopic video cameras (hereinafter referred to as "camera heads"), are most advantageously small and lightweight for ease of use by medical personnel, and typically incorporate either single or multiple solid-state imagers. Some special purpose endoscopes have integrated (built-in) solid-state imagers, which do not facilitate direct viewing of internal body cavities by medical personnel without an accompanying video imaging system and display. To achieve the desired size and weight, camera head and/or integrated endoscope-camera assembly electronics are typically separated physically from the majority of circuitry required to process and output high-quality, color video images.

Typically, endoscopic camera heads are sterilized prior to each use, because camera heads and endoscopes enter the "sterile field" during a surgical procedure. Camera control units ("CCUs"), which contain the majority of the electronic circuitry required to process video images, are typically not sterilized, and are placed on or in carts, or permanently wall-mounted. In known video imaging systems, interconnection is achieved by means of a cable, with usually one cable end permanently fixed to the camera head, while the other cable end is detachably connected to the CCU using a connector. Similar to the camera head itself, it is advantageous that cables be small in diameter and lightweight, but rugged enough to withstand repeated sterilization, accidental gurney wheel "run-over," and the like.

Known video imaging systems typically include at least one camera head with a fixed cable, and often either a CCU having various input connections or different CCUs for each camera type. The input connections to the CCU are keyed so that specific camera heads can only be connected to a specific one of various inputs or to a particular CCU that corresponds to that particular camera head specifications. Timing signals, video system function command signals, and camera head supply voltages are all generated in the CCU for transmission to the camera head. The advantage to this camera head arrangement is small size, lightweight and easy maneuverability. Disadvantageously, only camera heads requiring timing signals matched to the CCUs timing generator may be utilized with this arrangement. Therefore, new or differing camera heads utilizing different timing signals cannot be utilized.

Another disadvantage of known video imaging systems is that the various camera heads have differing cable structures based upon the camera head parameters. Each camera head typically is matched to its own specifically configured cable.

Existing interconnections between camera heads and CCUs typically comprise dedicated parallel wires to provide greater data carrying capacity. It is meant by "dedicated parallel wires" that each specific signal is transmitted by means of an individual wire, either single for power and control signals or shielded coax for image data, between a camera head and CCU. However, a disadvantage of providing dedicated parallel wires is that typically twenty to thirty separate lines are required to control, energize and receive image data from camera heads, with most signal lines requiring a dedicated connector pin. The more lines required, the greater the diameter, size and corresponding weight of the cable bundle. The larger this bundle becomes, the more likely it is to interfere with medical personnel's use of the video imaging system. Moreover, utilizing dedicated parallel wire type cabling is undesired when additional functionality is required and added to either the camera head or CCU. To accommodate this new functionality, additional wiring must be incorporated in the cable bundle, requiring equipment redesign and subsequent purchase by customers. Also, as video imaging systems develop, CCUs are becoming programmable for compatibility with various types of camera heads, are adding new control features and are processing different types of video signals.

Another aspect of video imaging systems is that undesired image "noise" can be encountered, due to stray electromagnetic signals being induced upon the wires of the cable bundle (commonly referred to as electromagnetic interference, "EMI"), and from signal "cross-talk" within the cable itself. Known video imaging systems utilize analog signals for transmitting video and other signals to or from camera heads and CCUs. These analog signals, especially image data, are very susceptible to EMI from surgical electro-cautery equipment and the like. The use of EMI shielding is prohibitive due to the added cost and subsequent cable size and weight increase. Moreover, the desired endoscopic camera head cable length itself (typically 10 feet or more) tends to induce noise as analog signals are propagated down its length.

Additionally, solid-state imaging devices of higher resolution are becoming available and commercially feasible for use in video imaging systems. As imagers increase in sophistication, greater amounts of image data must be transmitted by means of the interconnection cable between camera heads and CCUs, and thus higher speed data transmission means must be utilized.

What is desired, therefore, is to provide a video imaging system where interconnection of camera heads is not limited to only those camera heads compatible with the timing signals generated in the CCU. Rather, a video imaging system is desired that enables the CCU to process image data and receive control signals from, and to issue command signals to, many types of camera heads, each having differing timing signal requirements.

It is further desired to provide a video imaging system that is resistant to both internal and external electromagnetic interference that does not require utilization of heavy shielding. This advantageously will enable the use of a small diameter, lightweight cable.

It is further desired to provide a video imaging system enabling camera heads and CCUs to take advantage of new features and functions without requiring redesign and/or replacement of the system. Such a configuration would provide the ability to accommodate future video camera system improvements and adaptations as current technology limitations are overcome, without obsolescing initial customer investments in CCUs.

It is further desired to provide a video imaging system that enables the use of a single pair of wires for transmission of control, command and image data transmission from and to the camera head and the camera control unit.

SUMMARY OF THE INVENTION

These and other objects of the invention are achieved in one advantageous embodiment by providing a video imaging system comprising: a camera control unit for processing a digital image signal; a cable, connected to said camera control unit, for transmitting the digital image signal to said camera control unit; and a camera head, connected to said cable, for providing the digital image signal, said camera head including: an imager, for generating an analog image signal; a timing generator, for actuating said imager; a converter, for converting the analog image signal into the digital image signal; and a serializer, for serializing the digital image signal for transmission over said cable.

In another advantageous embodiment a video imaging system is provided comprising: a camera control unit for processing an image signal; a cable, connected to said camera control unit, for transmitting the image signal to said camera control unit; and a camera head, connected to said cable, for providing the image signal, said camera head including: an imager, for generating the image signal; and a timing generator, for actuating said imager.

In a further advantageous embodiment a video imaging system is provided comprising: a camera control unit for processing a digital image signal; a cable, connected to said camera control unit, for transmitting the digital image signal to said camera control unit; and a camera head, connected to said cable, for providing the digital image signal, said camera head including: an imager, for generating an analog image signal; and a converter, for converting the analog image signal into the digital image signal.

In yet another advantageous embodiment a video imaging system is provided comprising: a camera control unit for processing an image signal; a cable, connected to said camera control unit, for transmitting the image signal to said camera control unit; and a camera head, connected to said cable, for providing the image signal, said camera head including: an imager, for generating an image signal; and a serializer, for serializing the image signal for transmission over said cable.

In still another advantageous embodiment a video imaging system is provided comprising: a camera control unit for processing an image signal, a cable, connected to said camera control unit, for transmitting the image signal to said camera control unit, and a camera head, connected to said cable, for providing the image signal, said camera head including: an imager, for generating the image signal; and a processor.

In a further advantageous embodiment a video imaging system is provided having a small diameter, lightweight, universal cable configuration, utilizing low-voltage differential signals ("LVDS"). Although various other signal methods may be used, LVDS based architecture is preferred due to its low power consumption, high-speed data transfer rate, two-wire unidirectional connectivity, and high resistance to internal (cross-talk) and external electromagnetic interference. The cable architecture is designed to reliably transmit and receive data from different camera heads to CCUs, as well as accommodate the differing technical requirements of different camera heads.

The cable has also been provided to accommodate the use of programmable CCUs. For instance, a camera head is connected by means of the universal cable to a programmable CCU. Software executing on the programmable CCU verifies connection to the camera head and retrieves camera head information relating specifically to that camera head. Camera head information may include command and control data comprising: software programs, operating information, timing signal data, camera head identification information, camera use information and the like. Control signals include any signal transmitted from the camera head except image data, such as timing signals generated by the timing generator, and signals generated by the processor. Command signals include any signal transmitted from the camera control unit to the camera head.

The architecture of the universal cable also greatly increases the data carrying capacity of the cable connection between the various CCUs and the varying camera heads. This need for increased data carrying capacity can be achieved by means of data multiplexing, while still maintaining the desired small diameter, and weight of a single cable. What is meant by "data multiplexing" is that any single signal path can be utilized for transmitting multiple data streams on a time-sharing basis. The new cable architecture will also allow for a greater cable length while not sacrificing data carrying capacity or inducing signal noise.

In a further advantageous embodiment a video imaging system is provided where the digital camera head comprises at least one processing device used to receive parallel digital video data and compress the data into a digital serial data stream for reception by at least one digital serial driver; and to receive digital serial data from at least one digital serial receiver. The programming flexibility realized using at least one processing device (such as, but not limited to, field programmable gate arrays, computer programmable logic devices, digital signal processors, and microprocessors) provides the necessary speed, precision, and adaptability desired for endoscopic video camera applications. Moreover, camera head physical size, production costs, and power consumption considerations are further mitigated by using a processor based video data compression and conversion configuration, instead of using discrete multiplexing devices. Additionally, as imager technologies improve, the invention can be easily adapted, by means of programming revision, to further exploit those improvements.

The invention and its particular features and advantages will become more apparent from the following detailed description considered with reference to the accompanying drawings.

DETAILED DESCRIPTION OF THE INVENTION

Figure 1:
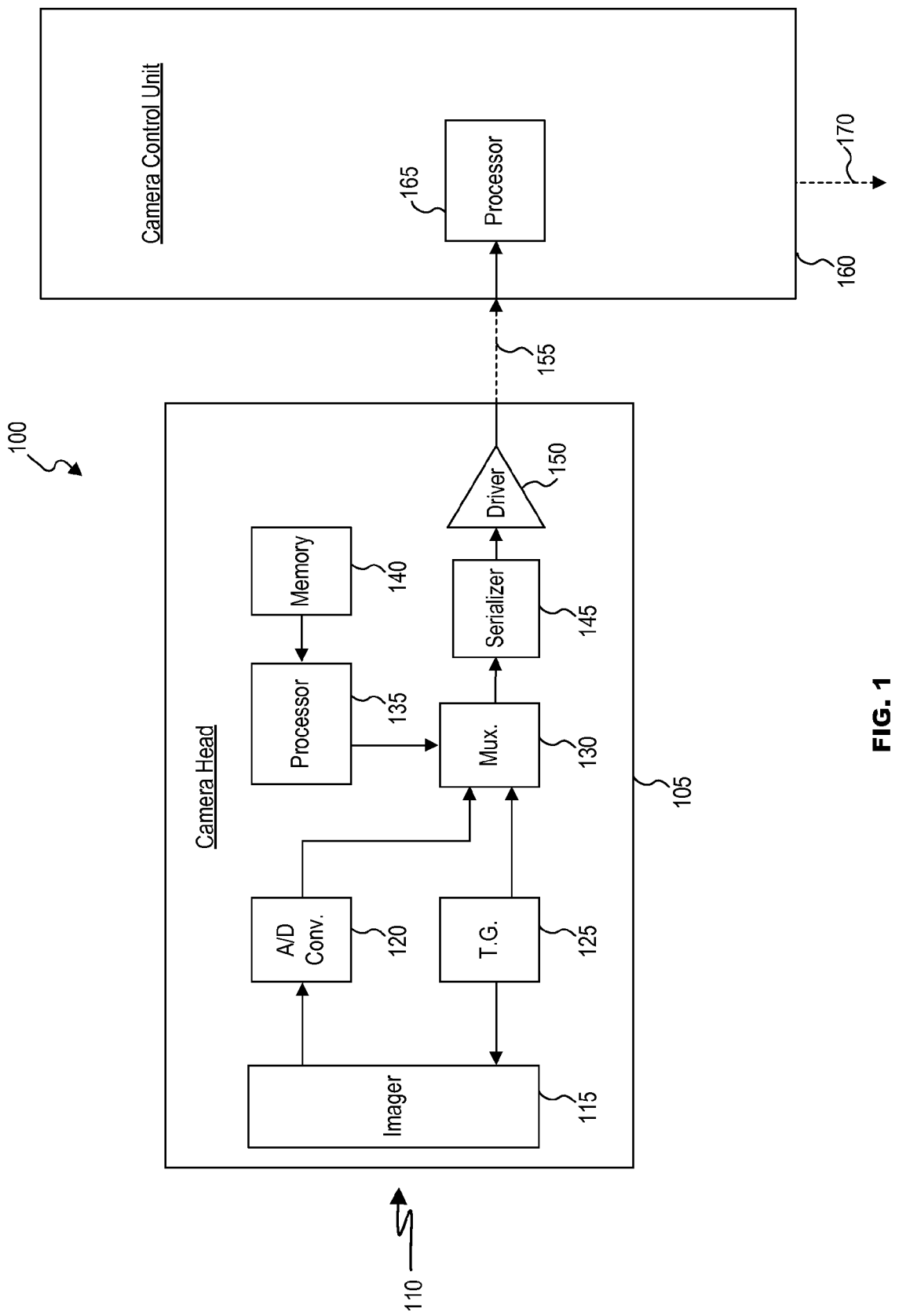
FIG. 1 is a block diagram illustrating an embodiment of the video imaging system—including the camera head, universal cable and camera control unit.

FIG. 1 illustrates an advantageous embodiment of the video imaging system 100. A camera head 105 is provided having an imager 115 for receiving photonic energy 110 reflected off a viewed object (not shown). The imager 115 utilizes timing signals generated in timing generator 125 to develop output analog image data corresponding to the received photonic energy 110. The imager 115 converts the received photonic energy 110 to output analog image data received by analog-to-digital converter 120. The analog-to-digital converter 120 in turn converts the received analog image data to digital image data. The digital image data is then fed into multiplexer 130. The timing generator 125 also provides an input to multiplexer 130. A processor 135, having access to a memory device 140 is also located in the camera head 105. The processor 135 may send camera information stored in memory device 140 to multiplexer 130. The multiplexer 130, multiplexes the various received input signals, generating a multiplexed digital signal. The output of multiplexer 130 is connected to serializer 145, also located in camera head 105. The output of serializer 145 is then connected to digital serial driver 150. The output of digital serial driver 150 is coupled to camera control unit 160 via coupling element 155. Camera control unit 160 processes the received signal via processor 165. The processor 165 utilizes timing signals generated in timing generator 125 to process the received image data in order to generate video output 170.

Figure 2:
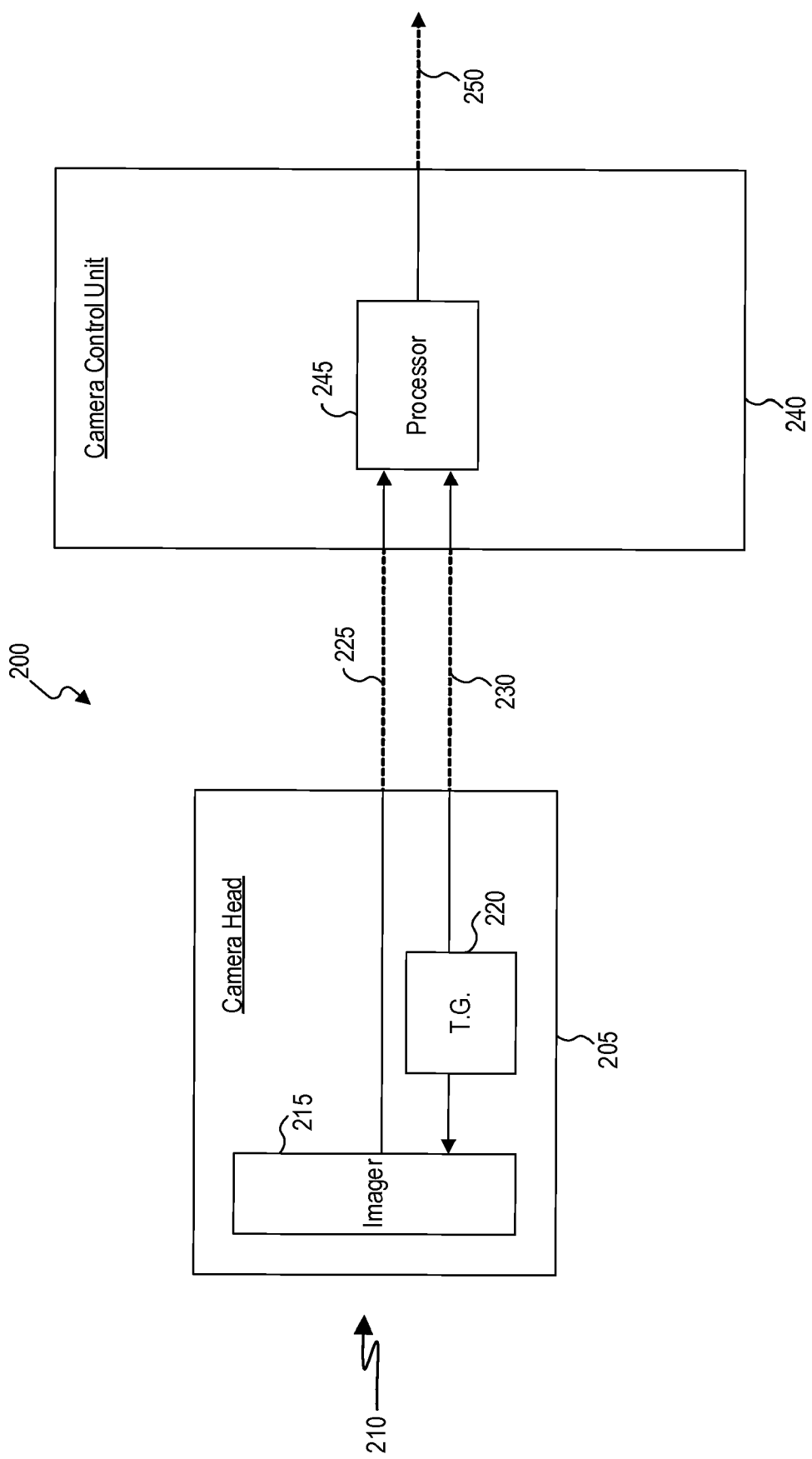
FIG. 2 is a block diagram illustrating an embodiment of the video imaging system—including the camera head, universal cable and camera control unit.

FIG. 2 illustrates an advantageous embodiment of the video imaging system 200. A camera head 205 is provided having an imager 215 for receiving photonic energy 210 reflected off a viewed object (not shown). The imager 215, located in camera head 205, utilizes timing signals generated in timing generator 220, also located in camera head 205, to develop output image data corresponding to the received photonic energy 210.

The output of imager 215 is coupled to processor 245, located in camera control unit 240, via coupling element 225. In addition, an output from timing generator 220 is coupled to processor 245, located in camera control unit 240, via coupling element 230. Processor 245 utilizes timing signals generated in timing generator 220 to process the received image data in order to generate video output 250.

Figure 3:
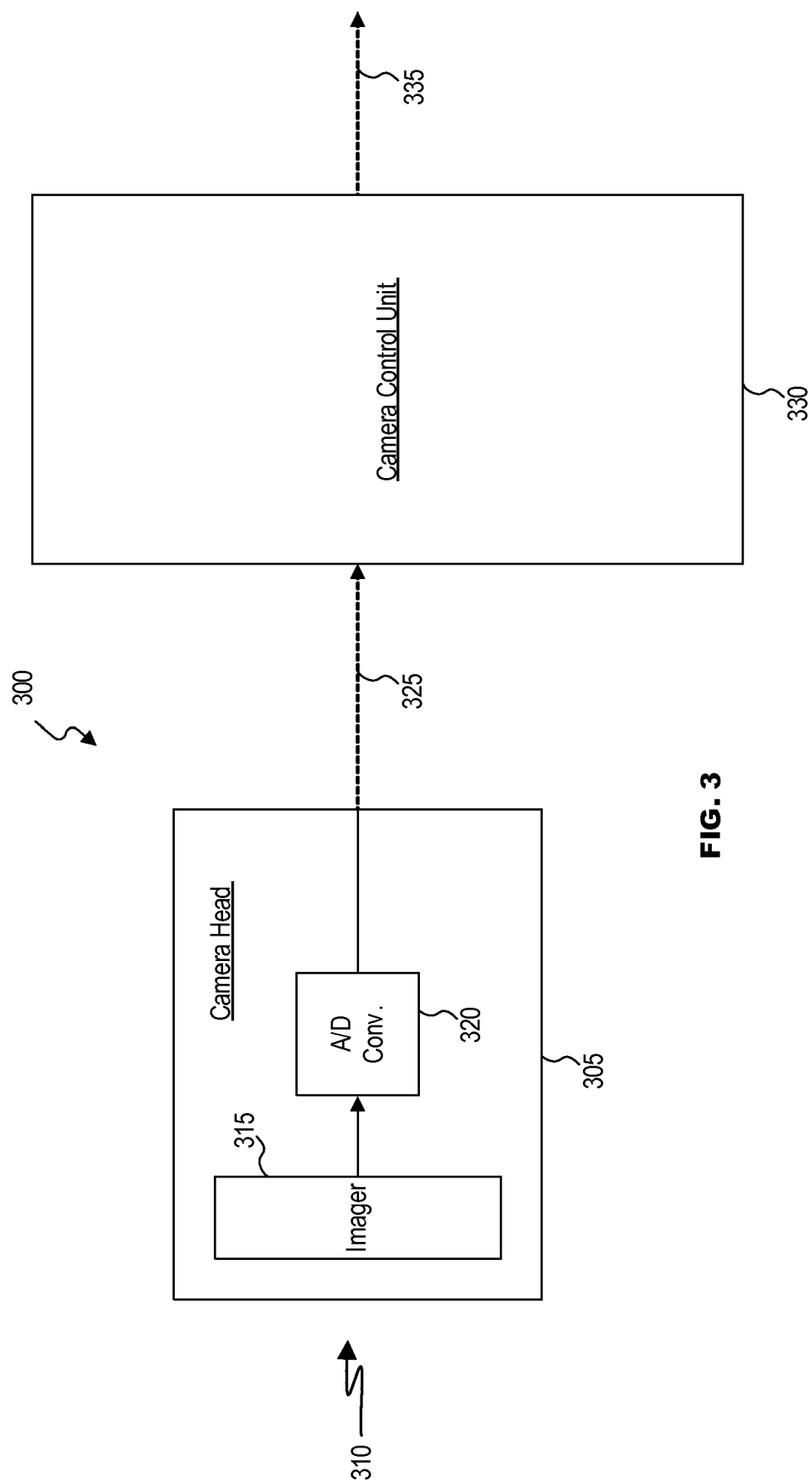
FIG. 3 is a block diagram illustrating an embodiment of the video imaging system—including the camera head, universal cable and camera control unit.

FIG. 3 illustrates an advantageous embodiment of the video imaging system 300. A camera head 305 is provided having an imager 315 for receiving photonic energy 310 reflected off a viewed object (not shown). The imager 315 develops output analog image data corresponding to the received photonic energy 310. The imager 315 converts the received photonic energy 310 to output analog image data received by analog-to-digital converter 320. The analog-to-digital converter 320 in turn converts the received analog image data to digital image data. The output of analog-to-digital converter 320 is then coupled to camera control unit 330 via coupling element 325. Camera control unit 330 processes the received digital image data to generate video output 335.

Figure 4:
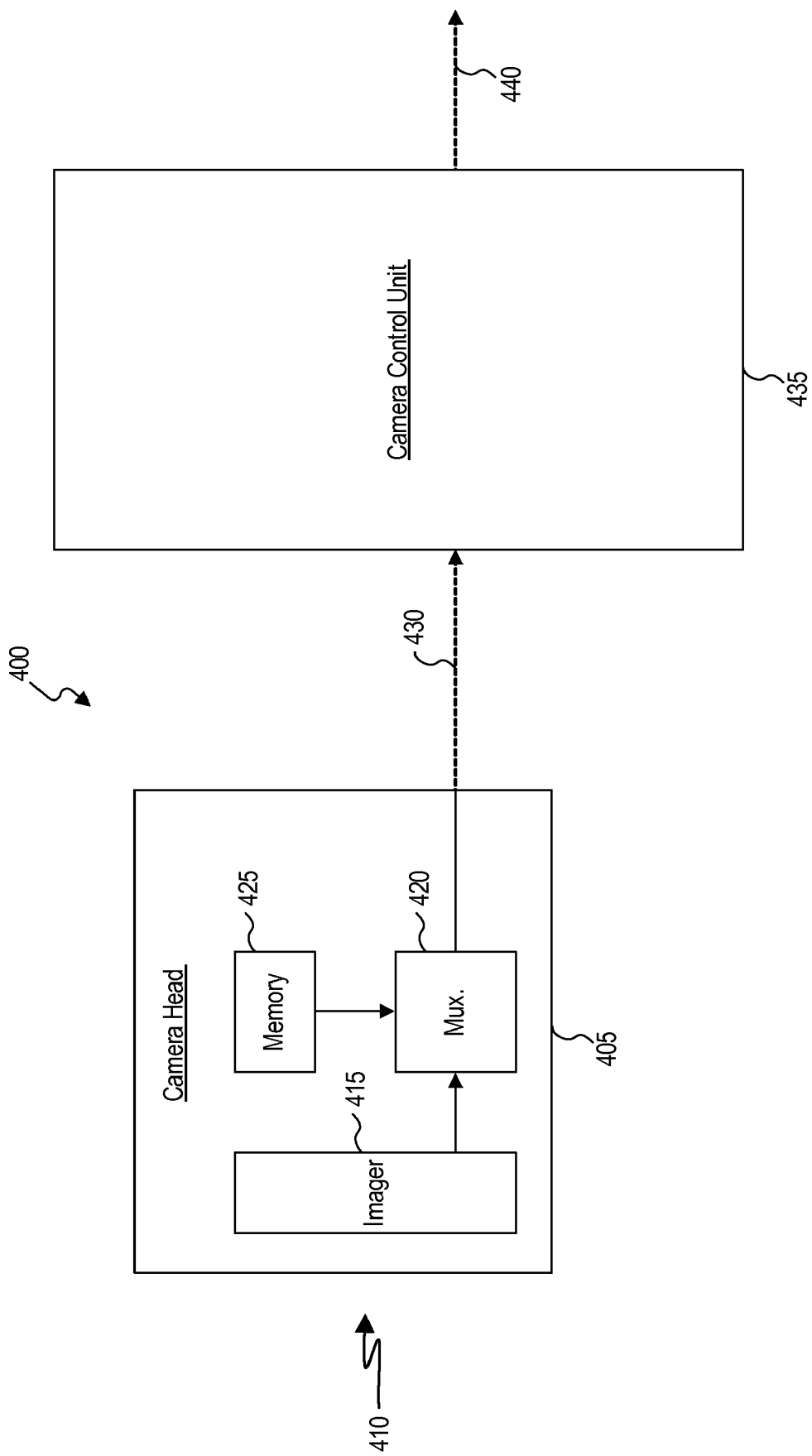
FIG. 4 is a block diagram illustrating an embodiment of the video imaging system—including the camera head, universal cable and camera control unit.

FIG. 4 illustrates an advantageous embodiment of the video imaging system 400. A camera head 405 is provided having an imager 415 for receiving photonic energy 410 reflected off a viewed object (not shown). The imager 415 develops output image data corresponding to the received photonic energy 410. The imager 415 converts the received photonic energy 410 to output image data received by multiplexer 420, also located in camera head 405. A memory device 425, located in the camera head 405, is also coupled to multiplexer 420. The multiplexer 420, multiplexes the various received input signals, generating a multiplexed signal. The output of multiplexer 420 is coupled to camera control unit 435 via coupling element 430. Camera control unit 435 processes the received signal to generate video output 440.

Figure 5:
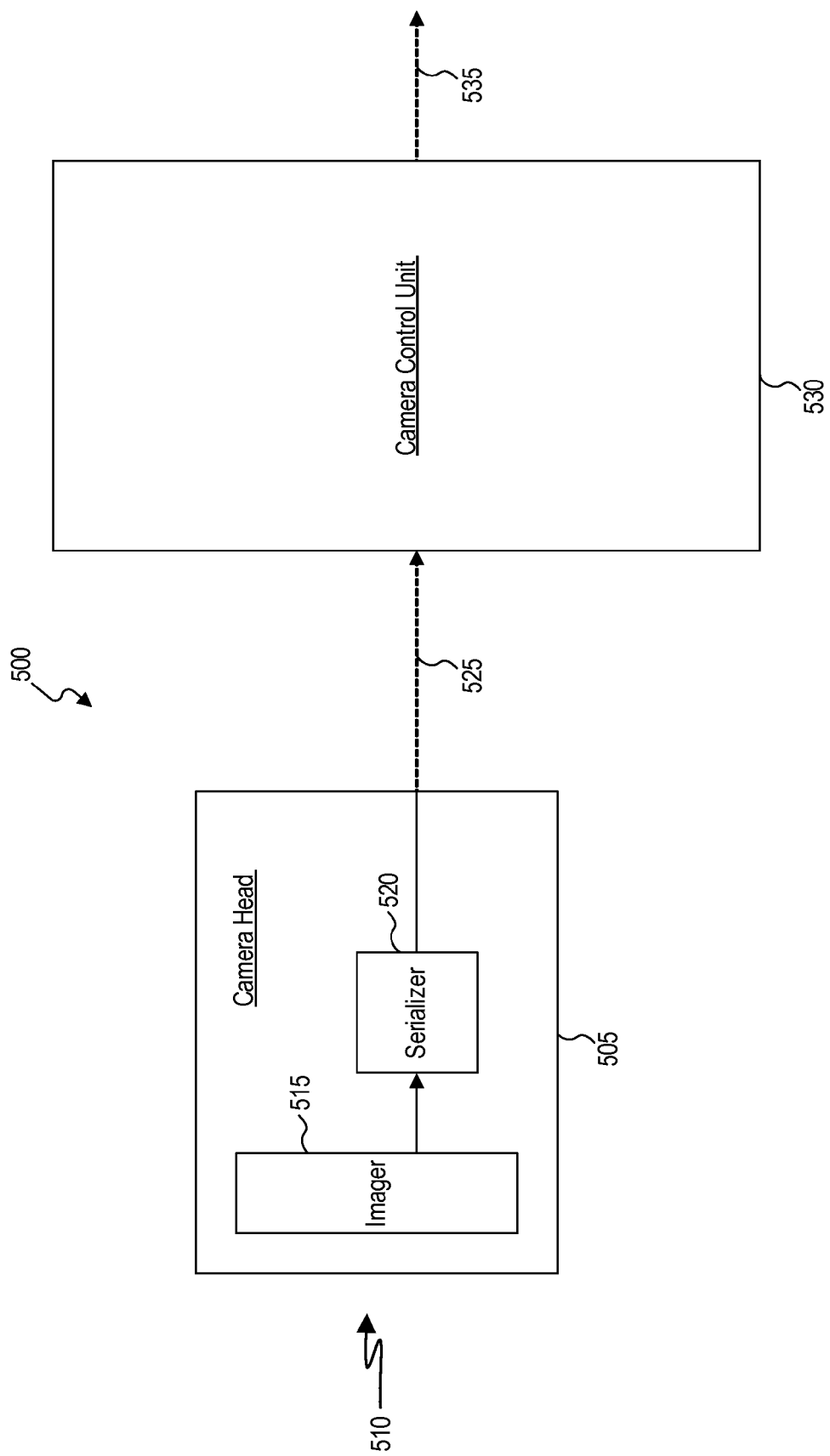
FIG. 5 is a block diagram illustrating an embodiment of the video imaging system—including the camera head, universal cable and camera control unit.

FIG. 5 illustrates an advantageous embodiment of the video imaging system 500. A camera head 505 is provided having an imager 515 for receiving photonic energy 510 reflected off a viewed object (not shown). The imager 515 develops output image data corresponding to the received photonic energy 510. The imager 515 converts the received photonic energy 510 to output image data received by serializer 520, also located in camera head 505. The output of serializer 520 is coupled to camera control unit 530 via coupling element 525. Camera control unit 530 processes the received signal to generate video output 535.

Figure 6:
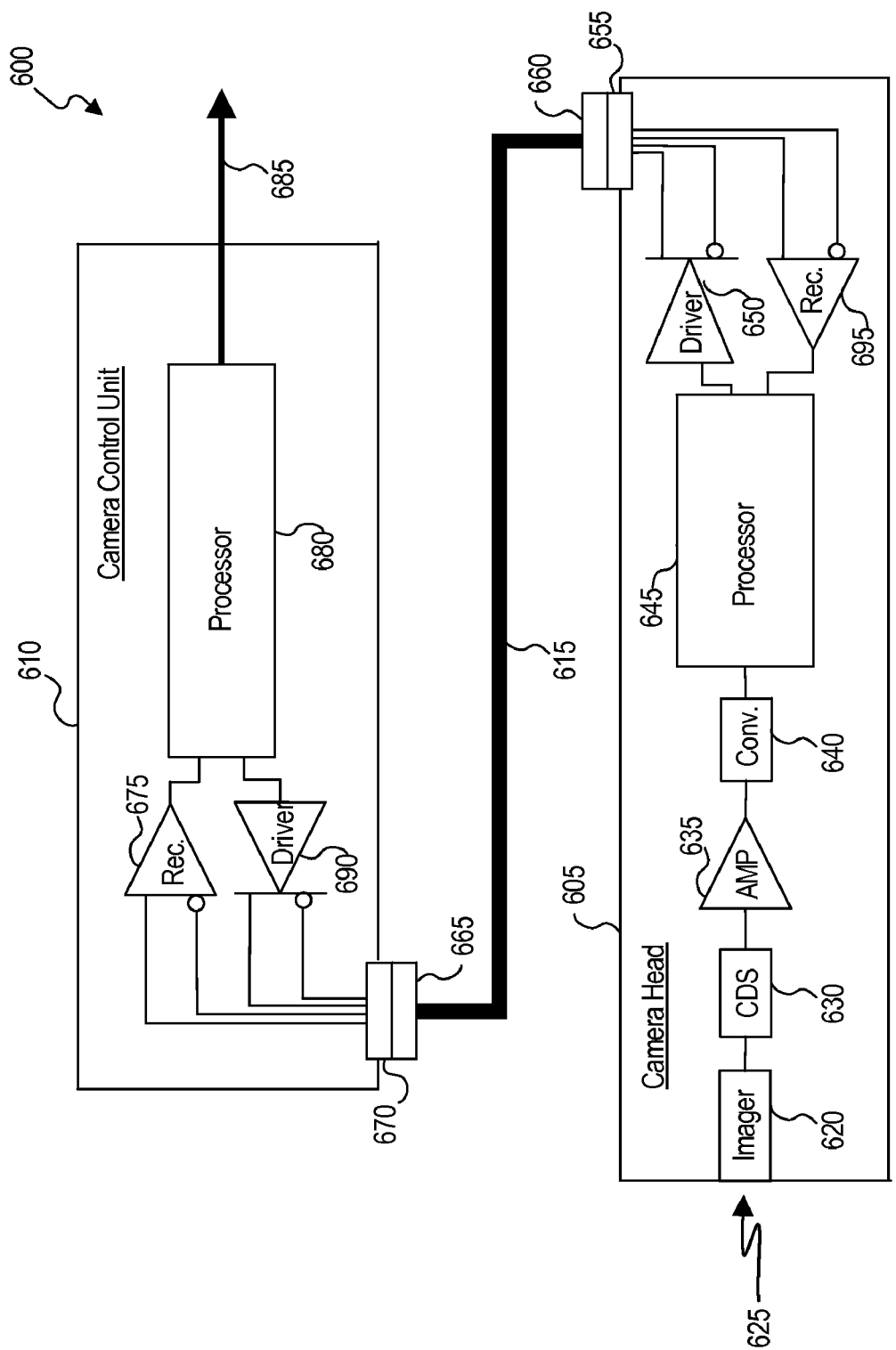
FIG. 6 is a block diagram illustrating an embodiment of the endoscopic system, the universal cable interconnecting a single imager camera head with a CCU.

FIG. 6 illustrates an advantageous embodiment the video imaging system 600, as applied to a single solid-state imager camera head 605, and CCU 610. The video imaging system 600 includes a universal cable 615, which connects camera head 605 to CCU 610. Solid-state imager 620 receives photonic energy 625 reflected off a viewed object (not shown). Imager 620, being a charge coupled device ("CCD"), charge injection device ("CID"), or complementary metal oxide semiconductor ("CMOS") device, or the like, converts the photonic energy into a representative analog voltage, which is received by correlated double sampler ("CDS") 630. Amplifier 635 receives the analog output of CDS 630. The output of amplifier 635 is analog image data varying in accordance with the output of imager 620 in reference to the gain level setting of amplifier 635. The analog image data output from amplifier 635 is received by analog-to-digital ("A/D") converter 640, which outputs a stream of digital image data (by means of a plurality of parallel lines) corresponding to the "varying" analog image data output by amplifier 635. CDS 630, amplifier 635, and A/D converter 640 can be discrete devices, but it is preferred that all be integrated into a single device, and more preferred to utilize a device such as, but not limited to, Exar, part no., XRD98L59 Image Digitizer, or National Semiconductor, part no. LM98501 or LM98503 Camera Signal Processors. Such integrated devices are in common use within the video camera head field.

Processor 645 receives the parallel digital image data output by A/D converter 640, to compress the data into a digital serial data stream for reception by digital serial driver 650. Processor 645 can be, but is not limited to, a processor type such as field programmable gate arrays, computer programmable logic devices, digital signal processors, and microprocessors. Processor 645 outputs digital serial image data, which is received by digital serial driver 650. Although various other digital serial drivers may be used, a low-voltage differential signal driver is preferred, for reasons previously detailed, and more preferred is to utilize a device such as, but not limited to, Texas Instruments, part no. SN65LVDS1 High-Speed Differential Driver. The output of digital serial driver 650 is connected to first connector 655.

Universal cable 615 is terminated at a second end with a second connector 660. To provide interconnection between camera head 605 and CCU 610 via universal cable 615, the second connector 660 is secured to first connector 655. Further, a third connector 665 is provided for securing to a fourth connector 670. The input to digital serial receiver 675 is connected to a fourth connector 670. Although various other digital serial receivers may be used (necessarily being compatible with digital serial driver 650), a low voltage differential signal receiver is preferred, for reasons previously detailed, and more preferred to utilize a device such as, but not limited to, Texas Instruments, part no. SN65LVDS2 High-Speed Differential Receiver. The output of digital serial receiver 675 is connected to image processing circuitry 680, for eventual output of image data 685. Image data 685 for display on a video monitor or other video equipment (not shown), as is common within the field.

A further function provided in this advantageous embodiment is the ability to send control and/or command signals to, and write information to the camera head 605 via processor 645. The input to digital serial driver 690 is connected to image processing circuitry 680 and the output of digital serial driver 690 is connected to the fourth connector 670. In this manner, information and data may be transmitted to the camera head 605 via the universal cable 615. In the camera head 605, the input to digital serial receiver 695 is connected to the first connector 655 for receiving the transmitted information and/or data from digital serial driver 690. In addition, the output to digital serial receiver 695 is connected to processor 645 to effect control and/or command signals and to store data.

Figure 7:
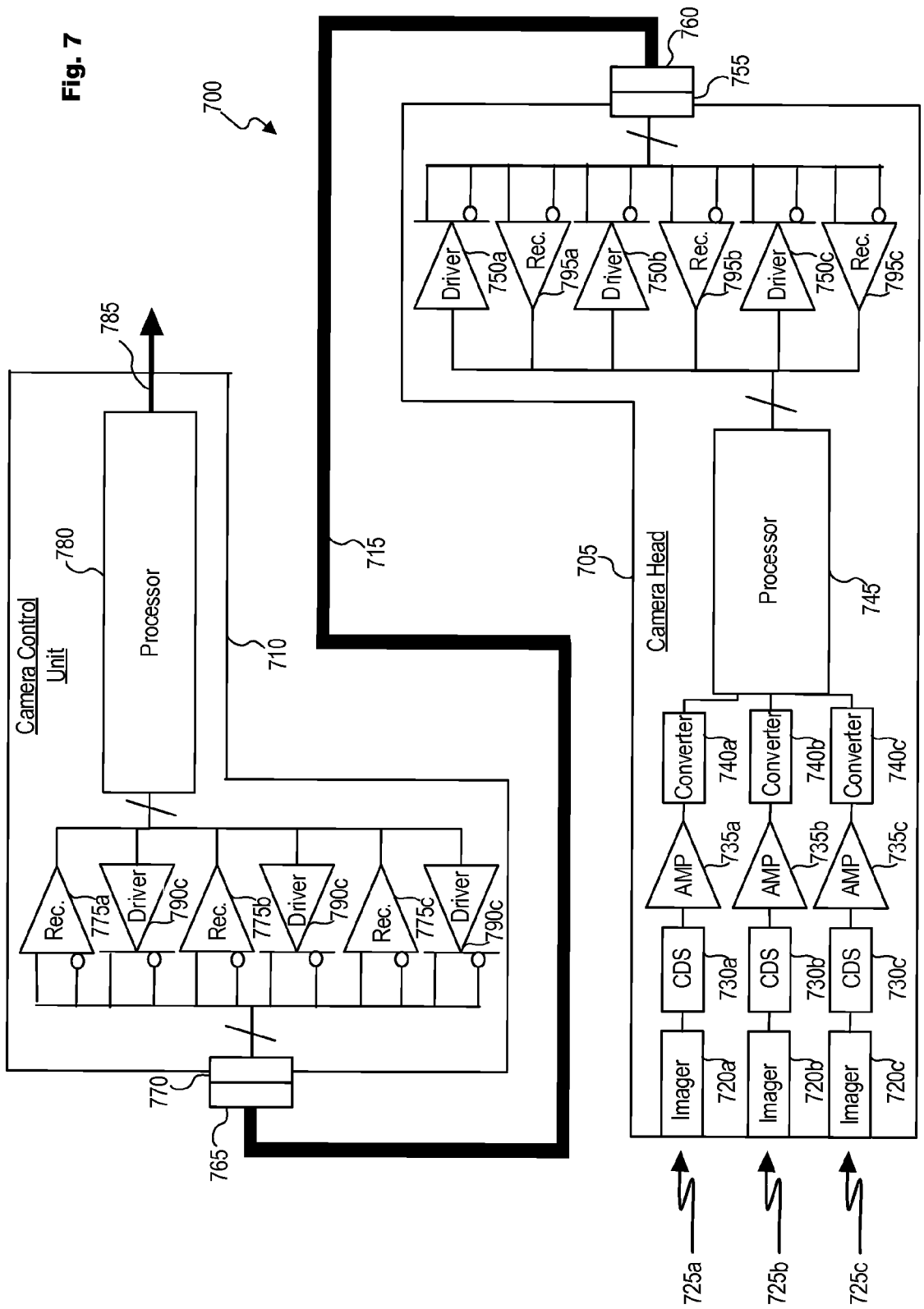
FIG. 7 is a block diagram illustrating an embodiment of the endoscopic system, the universal cable interconnecting a multiple imager camera head with a CCU.

FIG. 7 illustrates the video imaging system 700, as applied to a multiple solid-state imager camera head 705, and CCU 710. The video imaging system 700 includes, a universal cable 715, which connects camera head 705 to CCU 710. Common within the field, multiple imagers are affixed to a prism assembly (not shown), which splits received photonic energy (725a, 725b, and 725c) into three separate wavelength bands (red, blue and green, in the case of visible light camera systems), which are then detected by the solid-state imagers (720a, 720b, and 720c). This configuration produces higher resolution images than a single imager configuration. Solid-state imagers (720a, 720b, and 720c) receive photonic energy (725a, 725b, and 725c) from a prism assembly (not shown). Imagers (720a, 720b, and 720c) being a CCD, CID, or CMOS device, or the like, convert the photonic energy (725a, 725b, and 725c) into representative analog voltages, which are received by CDS (730a, 730b, and 730c). Analog outputs of CDS (730a, 730b, and 730c) are received by amplifiers (735a, 735b, and 735c). The output analog image data of amplifiers (735a, 735b, and 735c) vary in accordance with the output of imagers (720a, 720b, and 720c) in reference to the gain level setting of amplifiers (735a, 735b, and 735c). The analog image data output from amplifiers (735a, 735b, and 735c) is received by A/D converters (740a, 740b, and 740c), which each output a stream of digital image data (by means of a plurality of parallel lines) corresponding to the "varying" analog image data outputs by amplifiers (735a, 735b, and 735c). CDS 730a, amplifier 735a and A/D 740a (as well as CDS 730b and 730c, amplifiers 735b and 735c, and A/Ds 740b and 740c) can be discrete devices, but it is preferred that all be integrated into a single device, and more preferred to utilize a device such as, but not limited to, Exar, part no., XRD98L59 Image Digitizer, or National Semiconductor, part no. LM98501 or LM98503 Camera Signal Processors. Such integrated devices are in common use within the video camera field.

Processor 745 receives the parallel digital image data, to compress the data into a digital serial data stream for reception by digital serial drivers (750a, 750b, and 750c). Processor 745 can be, but is not limited to, a processor type such as field programmable gate arrays, computer programmable logic devices, digital signal processors and microprocessors. Processor 745 outputs digital serial image data, which is received by digital serial drivers (750a, 750b, and 750c). Although various other digital serial drivers may be used, low-voltage differential signal drivers are preferred, for reasons previously detailed, and more preferred is to utilize a device such as, but not limited to, Texas Instruments, part no. SN65LVDS1 High-Speed Differential Driver. The outputs of digital serial drivers (750a, 750b, and 750c) are connected to second connector 755.

Universal cable 715 is terminated with a first connector 760 at the first end. To provide interconnection between camera head 705 and CCU 710 via universal cable 715, first connector 760 is secured to second connector 755, and a third connector 765, which is terminated on the second end of cable 715, is secured to fourth connector 770. Digital serial receivers (775a, 775b, and 775c) inputs are connected to fourth connector 770. Although various other digital serial receivers may be used (necessarily being compatible with digital serial drivers (750a, 750b, and 750c), low voltage differential signal receivers are preferred, for reasons previously detailed, and more preferred is to utilize a device such as, but not limited to, Texas Instruments, part no. SN65LVDS2 High-Speed Differential Receiver. The outputs of digital serial receiver (775a, 775b, and 775c) are attached to video processing circuitry 780, for eventual output of video signal 785. Video signal 785 is intended to be displayed on a video monitor or other video equipment (not shown), as is common within the field.

A further function provided in this advantageous embodiment is the ability to send control and/or command signals to, and write information to the camera head 705 via processor 745. The input to digital serial drivers (790a, 790b, 790c) is connected to image processing circuitry 780 and the output of digital serial drivers (790a, 790b, 790c) is connected to fourth connector 770. In this manner, information and data may be transmitted to the camera head 705 via the universal cable 715. In camera head 705, the input to digital serial receivers (795a, 795b, 795c) is connected to second connector 755 for receiving the transmitted information and/or data from digital serial drivers (790a, 790b, 790c). In addition, the output to digital serial receivers (795a, 795b, 795c) is connected to processor 745 to effect control and/or command signals and to store data.

The video imaging systems 600 (700) in FIGS. 6 and 7 have been designed to accommodate anticipated future data carrying requirements. Endoscope systems will, most likely, continue to become more flexible. For instance, CCUs are becoming programmable for compatibility with various types of cameras, are adding new control features, and are processing differing image signals.

In view of this, the video imaging systems 600 (700) have been designed to effectively transmit data between different camera heads and CCUs in order to utilize programmable CCUs. As depicted in FIGS. 6 and 7, digital serial drivers 650 (750a, 750b and 750c) and digital serial receivers 675 (775a, 775b and 775c) provide this data capability. In like manner to digital serial drivers/receivers 650 (750a, 750b and 750c) and 675 (775a, 775b and 775c), various digital serial drivers and receivers may be utilized, but a low-voltage differential signal driver and receiver are preferred, for reasons previously detailed, and more preferred to utilize devices such as, but not limited to, Texas Instruments, part no. SN65LVDS1 High-Speed Differential Driver and part no. SN65LVDS2 High-Speed Differential Receiver.

As depicted in FIG. 7, digital serial drivers (750a, 750b and 750c; and 690a, 690b and 690c), and digital serial receivers (775a, 775b and 775c; 695a, 695b and 695c) are provided for expanded data and control capabilities as future video imaging system improvements are realized.

As depicted in FIGS. 6 and 7, to eliminate the need for a different cable type for each camera head configuration, the universal cable 615 (715) is designed to be compatible with a variety of camera heads. A generic universal cable 615 (715) would be used for both multiple and single image sensor cameras 605 (705). This would be accomplished by providing a universal cable 615 (715) with sufficient data carrying capacity to accommodate a multi-imager digital camera, as depicted in FIG. 7. If the same cable were utilized with a single imager digital camera, as depicted in FIG. 6, then the signal paths not being utilized would not be connected within the camera. Therefore, a single generic universal cable 615 (715) is usable with a variety of camera heads, eliminating the need to stock a specific cable for differing video imaging system types.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A video imaging system comprising:
   a camera head including an imager generating a stream of video data, at least one digital driver, a processor, and a memory device, accessible by said processor, containing camera head information;
   a cable; and
   a camera control unit coupled to said camera head via said cable and having at least one digital receiver;
   said camera control unit processing a stream of digital video data;
   wherein a plurality of camera heads are attachable to and controlled by said camera control unit.

2. The video imaging system according to claim 1 wherein said camera head further comprises a timing generator for generating a timing signal particular to said camera head, wherein the timing signal actuates said imager.

3. The video imaging system according to claim 2 wherein the timing signal is sent to said camera control unit.

4. The video imaging system according to claim 1 wherein said imager produces analog image data and said camera head further comprises a converter for converting the analog image signal to a digital image signal.

5. The video imaging system according to claim 1 wherein said camera head further comprises a multiplexer for generating a multiplexed signal, wherein the multiplexed signal includes the image signal and control signals.

6. The video imaging system according to claim 1 wherein said camera head further comprises a serializer for serializing the image signal.

7. The video imaging system according to claim 1 wherein the camera head information is used to format said camera control unit.

8. The video imaging system according to claim 1 wherein the digital driver utilizes Low-Voltage Differential Signals.

9. The video imaging system according to claim 1 wherein the digital receiver utilizes Low-Voltage Differential Signals.

* * * * *